United States Patent [19]
Yamada et al.

[11] Patent Number: 5,990,480
[45] Date of Patent: Nov. 23, 1999

[54] KLM MARKER DISPLAY CONTROLLER FOR EPMA OR THE LIKE

[75] Inventors: Hiroyuki Yamada; Masaki Saito, both of Tokyo, Japan

[73] Assignee: JEOL Ltd., Tokyo, Japan

[21] Appl. No.: 08/964,657

[22] Filed: Nov. 5, 1997

[30] Foreign Application Priority Data

Nov. 6, 1996 [JP] Japan ................................. 8-293546

[51] Int. Cl.[6] ............................................. H01J 37/256
[52] U.S. Cl. ............................................. 250/310
[58] Field of Search ............................................. 250/310

[56] References Cited

U.S. PATENT DOCUMENTS

| | | | |
|---|---|---|---|
| 3,146,347 | 8/1964 | Ziegler | 250/310 |
| 4,439,680 | 3/1984 | Broadhurst | 250/310 |
| 4,885,465 | 12/1989 | Nagatsuka et al. | 250/310 |
| 4,988,872 | 1/1991 | Nagatsuka et al. | 250/310 |

*Primary Examiner*—Jack I. Berman
*Attorney, Agent, or Firm*—Webb Ziesenheim Logsdon Orkin & Hanson, P.C

[57] ABSTRACT

A KLM marker display controller for use with an electron probe microanalyzer or the like. This controller has a marker information table holding positional information about markers, line species and orders in tabular form for each element. When the human operator specifies an element, line species and orders through a marker-specifying portion to display markers, positional information about the line species of this element is read from the marker information table and the markers are displayed at positions determined by the positional information and the orders.

2 Claims, 4 Drawing Sheets

| ELEMENTS | CHARACTERISTIC X-RAY LINES | WAVE-LENGTHS | INTENSITIES (HEIGHTS) |
|---|---|---|---|
| 00000001  Fe | $K\alpha_1$ | | 100 |
| | $K\alpha_2$ | | 50 |
| 00001001  Cu | | | |

FIG. 2(A)

| ELEMENTS | ADDRESSES |
|---|---|
| Fe | 00000001 |
| Cu | 00001001 |

FIG. 2(B)

| CHARACTERISTIC X-RAY LINES | COLORS |
|---|---|
| $K\alpha_1$ | RED |
| $K\alpha_2$ | ORANGE |
| $L\alpha$ | BLUE |

FIG. 2(C)

KLM MARKER DISPLAY CONTROLLER FOR EPMA OR THE LIKE

FIELD OF THE INVENTION

The present invention relates to an electron probe microanalyzer (EPMA) or the like for collecting X-ray spectra and, more particularly, to a KLM marker display controller for displaying KLM markers on an X-ray spectrum collected by the EPMA to denote the names and positions of elements.

BACKGROUND OF THE INVENTION

Electron probe microanalysis (EPMA) is a method for directing a sharply focused electron beam at a specimen surface, dispersing characteristic X-rays emanating from the irradiated surface by the use of an analyzing crystal and detecting the dispersed X-rays by an X-ray detector to analyze the elements contained in the specimen. Such characteristic X-rays are some of K, L, M lines, etc., depending on the element. The K family includes numerous line species such as $K\alpha_1$, $K\alpha_2$, . . . , $K\beta_1$, etc. In electron probe microanalysis where X-rays are spectrally dispersed through the use of an analyzing crystal, X-rays due to higher-order reflections such as 2nd-, 3rd- and 4th-order lines are observed, as well as the 1st-order line produced by the 1st-order reflection, because of the nature of spectral dispersion by the analyzing crystal. Therefore, many characteristic X-ray line peaks are often observed to overlap each other on the X-ray spectrum.

The operator performs the following steps as one method of examining what elements are contained in the specimen. The operator watches the obtained X-ray spectrum on the chart and estimates the presence of one element. The element should be present at some location on the spectrum. Then, he or she examines X-ray line peaks observed near this location and judges whether this element is present. When some element is specified, if some markers indicating the positions at which the characteristic X-rays emitted from the element should appear are displayed on the spectrum, then convenience is offered. An energy-dispersive X-ray spectrometer (EDS) attached to a scanning electron microscope (SEM) has heretofore used KLM markers. Therefore, the function of these KLM markers may be applied to the electron probe microanalyzer. However, electron probe microanalysis has higher-order lines and better wavelength resolution than energy-dispersive X-ray spectrometry. Therefore, more line species are detected. Consequently, if data about higher-order lines are simply added to the KLM markers for EDS, the following problems take place.

FIG. 5 is a diagram representing an example of display of such KLM markers. X-ray spectra collected by EPMA are observed to contain numerous line species and characteristic X-rays of various orders for each element. Where plural elements are specified and their respective KLM markers are displayed, it follows that numerous markers denoting the characteristic X-rays emanating from the elements are intermingled. Therefore, the markers for the characteristic X-rays originating from the element of interest are not easy to discern or recognize.

SUMMARY OF THE INVENTION

The present invention is intended to solve the foregoing problem. It is an object of the invention to provide a technique for displaying characteristic X-rays arising from an element of interest in an easily recognizable form.

This object is achieved by a KLM marker display controller for use with an electron probe microanalyzer (EPMA) or the like. This microanalyzer collects X-ray spectra from a specimen and displays the spectra on a chart. The names of elements contained in the specimen and the positions of the elements are indicated by KLM markers on each X-ray spectrum. This KLM marker display controller is characterized in that it has a storage means and a control means. The storage means has a marker information table that holds positional information about lines species in tabular form for each element. When a human operator specifies an element, line species, and orders to display markers, the control means acts to read positional information about the line species of this element from the marker information table and to display markers at positions represented by the positional information.

Other objects and features of the invention will appear in the course of the description thereof, which follows.

BRIEF DESCRIPTION OF THE DRAWINGS

FIGS. 2(A)–2(C) are tables illustrating the structure of a marker information storage portion of the KLM marker display controller shown in FIG. 1;

DESCRIPTION OF THE PREFERRED EMBODIMENTS

Figure 1:
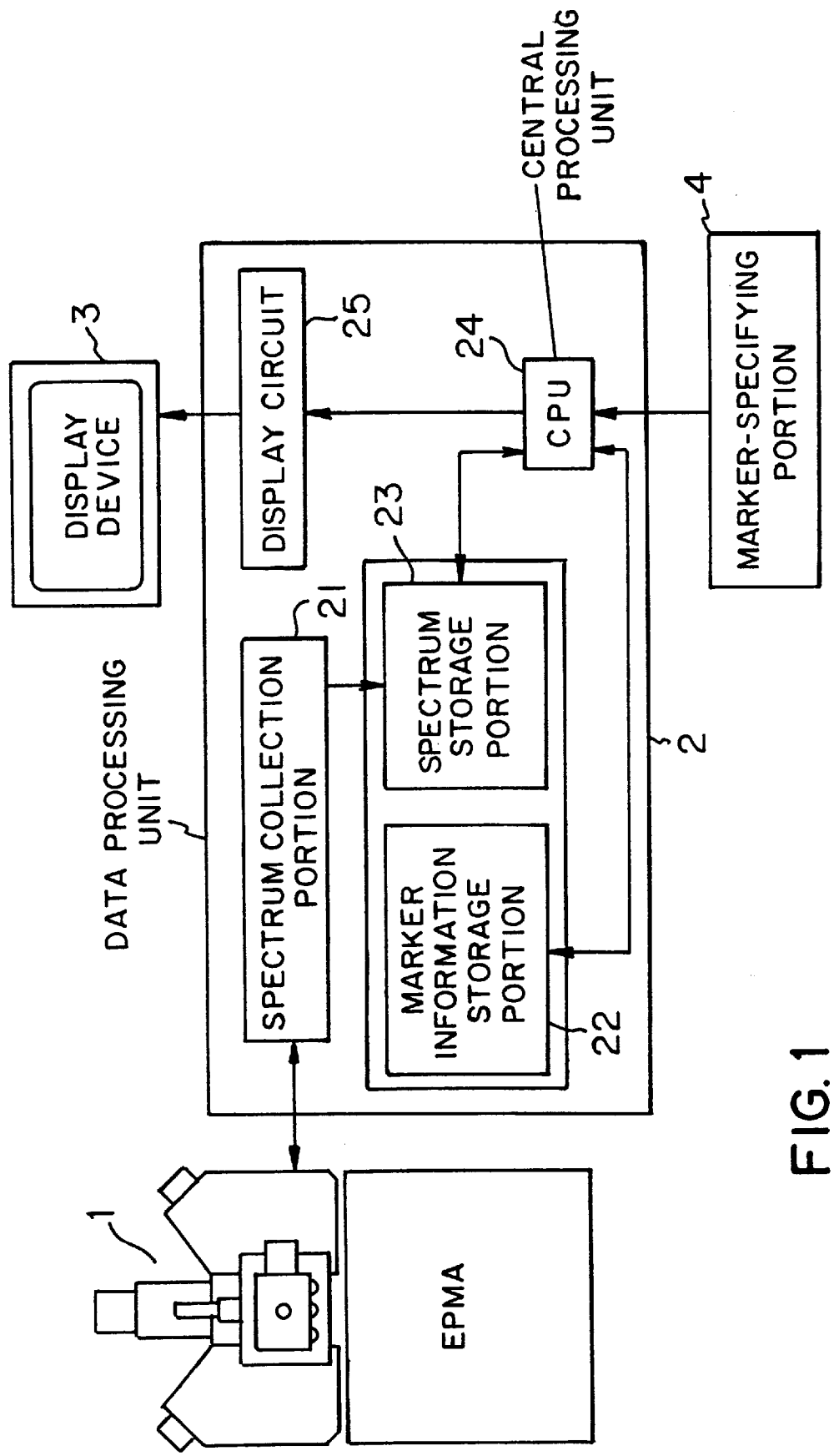
FIG. 1 is a block diagram of a KLM marker display controller for use with an electron probe microanalyzer (EPMA) or the like, the controller being built in accordance with the present invention.

Referring to FIG. 1, there is shown an electron probe microanalyzer (EPMA). The body of the microanalyzer, generally indicated by reference numeral 1, is interfaced to a data processing unit 2 constituting a KLM marker display controller embodying the concept of the present invention. The data processing unit 2 includes a marker-specifying portion 4, a spectrum collection portion 21, a marker information storage portion 22, a spectrum storage portion 23, a central processing unit (CPU) 24 and a display circuit 25. A display device 3 is connected with the data processing unit 2.

The body of the microanalyzer 1 includes an electron gun producing an electron beam which is sharply focused onto a specimen by a condenser lens and an objective lens. The irradiated portion of the specimen emits X-rays, which in turn are dispersed by an analyzing crystal. The dispersed X-rays are detected by a detector.

The data processing unit 2 accepts X-ray signals detected by the body 1 of the microanalyzer and processes the accepted signals to create spectra. The data processing unit 2 has the spectrum collection portion 21, the marker information storage portion 22, the spectrum storage portion 23, the CPU 24 and the display circuit 25 described above. The spectrum collection portion 21 collects data about X-ray spectra by controlling the physical apparatus comprising the EPMA 1. The collected data is stored in the spectrum storage portion 23. The marker information storage portion 22 consists of a hard disk or other storage device for storing information about KLM markers. The CPU 24 performs processing to display spectral data on the viewing screen of the display device 3 after reading the data from the spectrum storage portion 23. When the human operator operates the marker-specifying portion 4 to display desired markers, the CPU 24 reads information about the KLM markers from the marker information storage portion 22 and makes selections according to the specified element, line species and orders. The display circuit 25 superimposes KLM markers on the X-ray spectrum displayed on the viewing screen of the display device 3. Elements, line species and orders are selectively displayed according to the contents of the operator's designation.

Figure 3:
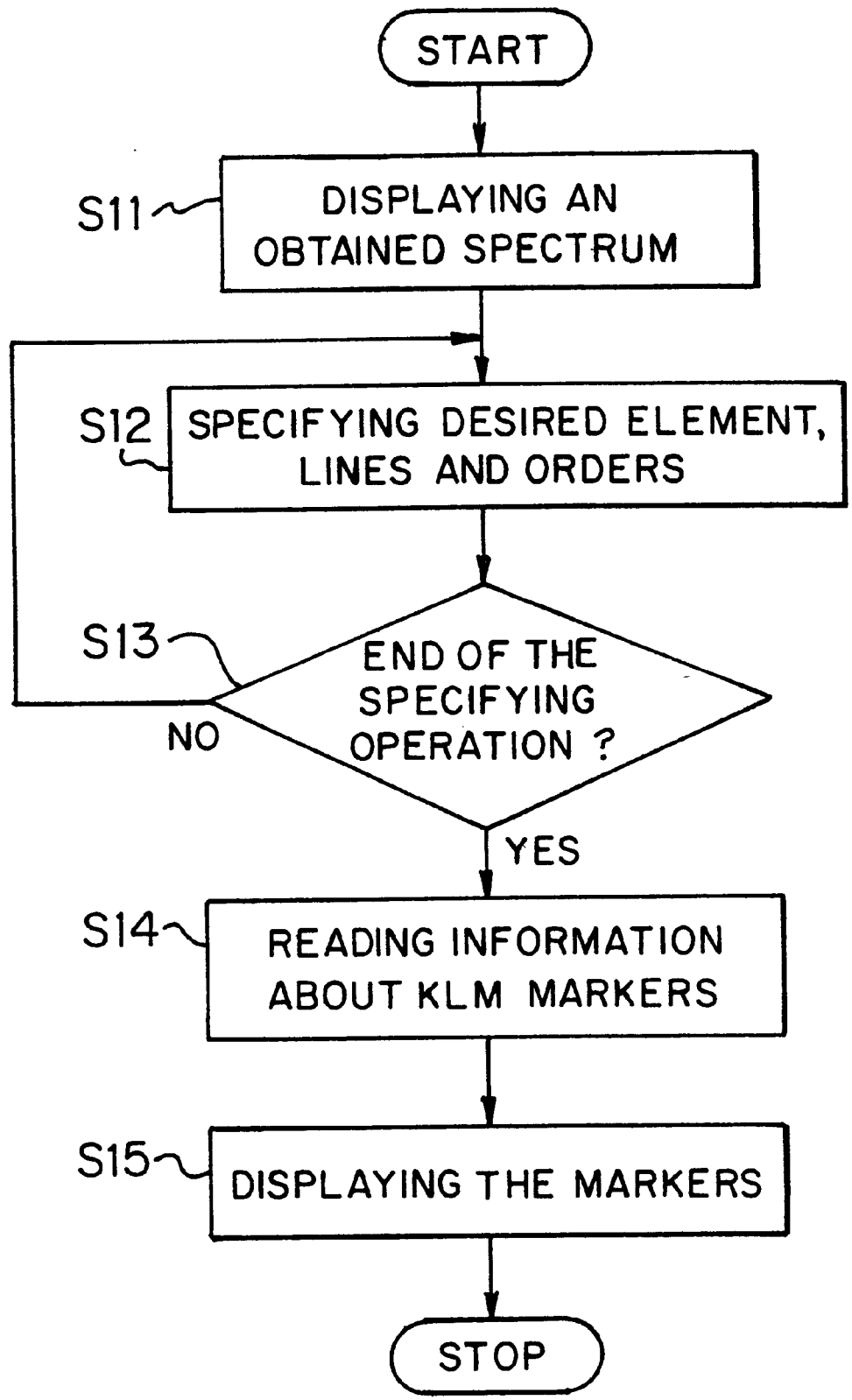
FIG. 3. is a flowchart illustrating processing performed by the KLM marker display controller shown in FIG. 1 when an element is specified.
Figure 4A:
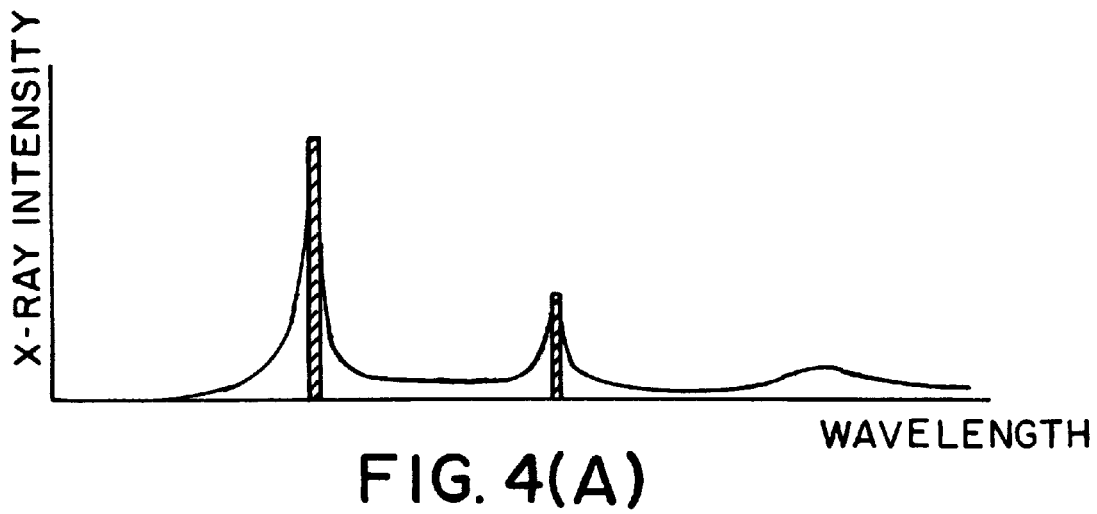
FIGS. 4(A) and 4(B) are diagrams illustrating examples of KLM markers displayed under control of the KLM marker display controller shown in FIG. 1.
Figure 4B:
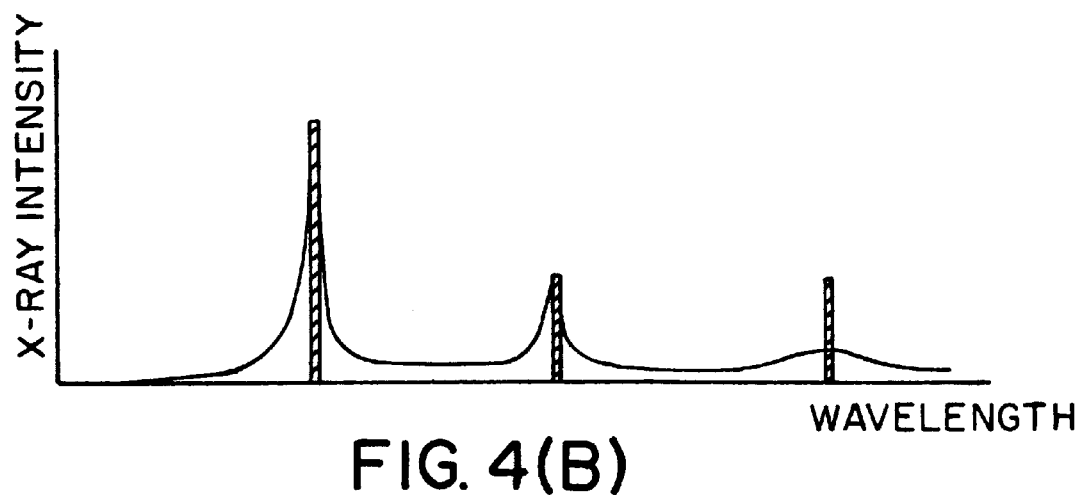

Information about the KLM markers and examples of display of the information are now described in detail. FIGS. 2(A)–2(C) show examples of the structure of the marker information storage portion 2 described above. FIG. 3 is a flowchart illustrating processing performed to display KLM markers according to the contents of the operator's designation. FIGS. 4(A) and 4(B) show examples of KLM markers displayed in accordance with the invention.

The marker information storage portion 22 stores data about KLM markers in tabular form as shown in FIG. 2(A). The table contains information about the characteristic X-rays (line species) from each element (such as Fe or Cu), wavelengths (i.e., information about the positions of the markers) of these characteristic X-rays and numerical values indicating the heights of the displayed markers. The storage portion 22 may also have a table showing elements indicated by KLM markers and corresponding memory addresses, as shown in FIG. 2(B). Furthermore, the storage portion 22 may have a table representing the relation between each characteristic X-ray line and the attributes of display, such as colors, as shown in FIG. 2(C).

The line species of the characteristic X-rays are $K\alpha_1$, $K\alpha_2, \ldots, K\beta_1, \ldots, L, M, \ldots$, etc. that have different wavelengths as mentioned previously. With respect to the heights of displayed markers, the X-ray intensity of some characteristic X-ray lines (e.g., $K\alpha_1$ line) of an element is taken to be 100. Taking this intensity as a standard intensity, the heights of the markers are set according to the relative intensities of other characteristic X-rays from the same element. With respect to orders, if the line is the 3rd-order X-line, for example, it is observed at a wavelength three times the wavelength of that characteristic X-ray. In other words, they are observed at wavelengths that are larger than the original wavelengths by factors equal to the orders. Therefore, these apparent wavelengths can be easily calculated by multiplying the original wavelengths by their respective orders. Consequently, it is not necessary to store these apparent wavelength values in the table of information about the KLM markers.

If the operator specifies element, line species and orders as marker-specifying information through the marker-specifying portion 4, the CPU 24 fetches wavelengths and heights corresponding to the element and line species from the table (as shown in FIGS. 2(A)–2(C)) of the information about the KLM markers, the table being stored in the marker information storage portion 22. The CPU calculates the apparent wavelengths by multiplying the original wavelengths by their respective order and transfers the fetched and calculated data to the display circuit 25. As a result, KLM markers associated with the specified element are superimposed on the X-ray spectrum.

Referring to FIG. 3, processing for displaying KLM markers is performed in the manner described below. The apparatus of the EPMA 1 is controlled to collect X-ray spectral data. A spectrum is created according to this data and displayed (step 11). Watching this spectrum, the operator specifies the desired element, line species and orders via the marker-specifying portion 4. Then, markers to be displayed according to the specified element, line species and orders are registered (step 12). Where plural elements are specified, the processing described thus far is repeatedly carried out. When "end of the specifying operation" is keyed in, the setting operation ends (step 13). Then, information about KLM markers associated with the set element, line species and orders is read from the marker information storage portion 22 (step 14). Finally, these KLM markers are displayed on the spectrum (step 15).

Normally, as the reflection order number increases, the intensity of the reflecting radiation decreases and becomes more difficult to detect. Therefore, it is only necessary to take account of up to some order. For example, it seems that specifying some value n and displaying X-ray lines up to order n is an appropriate method. In practice, however, even-order reflections are weaker than odd-order reflections, according to the kind of the analyzing crystal or other conditions, or even-order reflections are not reflected at all. Otherwise, 2nd, 3rd and 4th lines are weaker, but 5th, 6th and 7th lines are observed to be stronger. Hence, the above-described method is not always appropriate.

In a spectral range of interest, if the markers denoting certain orders of X-rays originating from some element are not displayed, then the spectrum often may be more easily seen. Suppose a specimen contains copper (Cu), titanium (Ti) and phosphorus (P). It is assumed that the Ti concentration is sufficiently higher than the Cu concentration and that the P concentration is quite low. The presence of these elements is now to be examined. The $K\alpha$ line of Cu has a wavelength of 1.542 Å. $K\beta_1$, line has a wavelength of 1.392 Å. The $K\alpha$ line of Ti has a wavelength of 2.750 Å and the $K\beta_1$ line has a wavelength of 2.514 Å. The $K\alpha$ line of P has a wavelength of 6.155 Å and the $K\beta_1$ line has a wavelength of 5.804 Å. Where the presence of Cu is examined, it is only necessary to investigate the $K\alpha$ and $K\beta_1$ lines of Cu, irrespective of Ti and P. In this case, no problem takes place at all. Where Ti is investigated, a problem may occur because the 2nd-order line of the $K\beta_1$ line (2×1.392 Å=2.784 Å) of Cu exists near the $K\alpha$ line (2.750 Å) of Ti. However, the $K\beta_1$, line of Cu is about 10 times weaker than the $K\alpha$ line of Cu. Furthermore, the Ti concentration is high in this case. In consequence, the peaks of the characteristic X-rays originating from Ti can be observed clearly. Therefore, if the marker indicating the 2nd-order line of Cu is not displayed, then the spectrum is made less complex and can be more easily interpreted. On the other hand, in the case of P, the 4th-order line (4×1.542 Å=6.168 Å) of Cu is present near the $K\alpha$ line (6.155 Å). Furthermore, the concentration of P is very low. Therefore, it is necessary to clearly distinguish between these two lines. In the example given thus far, markers are attached to the 1st- and 4th-order lines of Cu. No marker is attached to the 2nd-order line thus avoiding complicating the spectrum.

Figure 5:
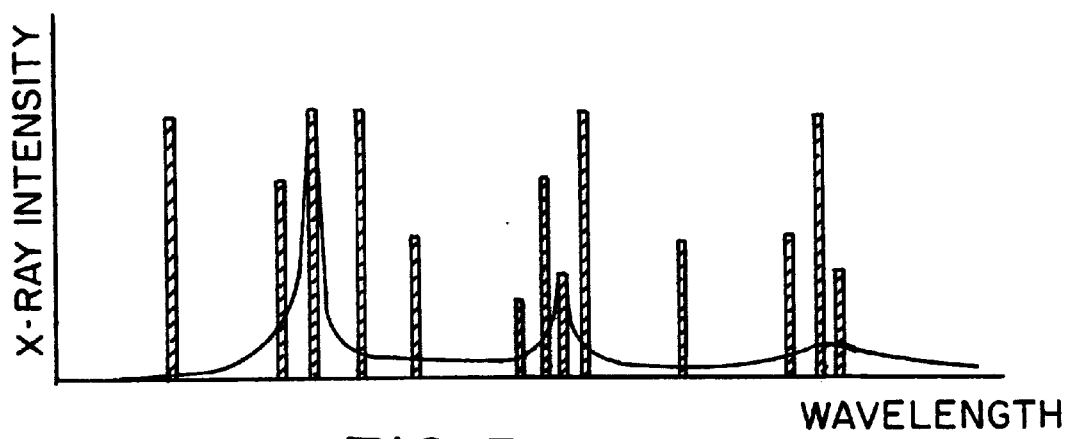
FIG. 5 is a diagram illustrating KLM markers displayed by the prior art techniques.

In this way, with the ordinary method, a number of markers are displayed as shown in FIG. 5, thus complicating the spectrum. In the processing in accordance with the invention, attention is paid to only selected lines and markers are attached to them as shown in FIGS. 4(A) and 4(B).

It is to be noted that the present invention is not limited to the embodiment described above but rather various changes and modifications are possible. For example, in the embodiment described above, markers are displayed on an X-ray spectrum obtained by EPMA (electron probe microanalysis). Obviously, the invention is also applicable to the case where markers are displayed on an X-ray spectrum created by a scanning electron microscope (SEM) fitted with a wavelength-dispersive X-ray spectrometer (WDS). Furthermore, in the above embodiment, desired element, line species and orders are specified, but it is also possible to specify other combinations of data (such as element and line species or element and orders).

As can be understood from the description provided thus far, even where plural elements are specified, markers indicating the line species and orders of a certain element can be displayed selectively by specifying some line species and orders. If the characteristic X-rays of some elements exist in close proximity and thus are difficult to interpret, the spectrum can be clarified. Also, the reliability of the analysis can be improved.

Having thus described our invention with the detail and particularity required by the Patent Laws, what is desired protected by Letters Patent is set forth in the following claims.

What is claimed is:

1. A KLM marker display controller for displaying markers indicating names and positions of elements on an X-ray spectrum obtained by an electron probe microanalyzer or the like, said KLM marker display controller comprising:

a storage means having a marker information table that holds spectrum position information about line species in tabular form for each element; and a control means enabling a human operator to individually select one or more elements, lines species thereof and orders to display one or more markers, said control means reading spectrum position information about the line species of an element from said marker information table and displaying said one or more markers at positions determined by said spectrum position information and the orders.

2. A KLM marker display controller for displaying markers indicating names and positions of elements on an X-ray spectrum obtained by an electron probe microanalyzer or the like, said KLM marker display controller comprising:

a storage means having a marker information table that holds information relating to spectrum positions and relative intensities of line species in tabular form for each element; and a control means enabling a human operator to specify an element, line species and order to one or more display markers, said control means reading information relating to spectrum position and relative intensity of line species of this element from said marker information table and displaying markers at positions determined by said information and the orders.

* * * * *